(12) United States Patent
Callol et al.

(10) Patent No.: US 6,174,329 B1
(45) Date of Patent: Jan. 16, 2001

(54) PROTECTIVE COATING FOR A STENT WITH INTERMEDIATE RADIOPAQUE COATING

(75) Inventors: Joseph R. Callol, San Francisco; John Y. Yan, Sunnyvale, both of CA (US)

(73) Assignee: Advanced Cardiovascular Systems, Inc., Santa Clara, CA (US)

(*) Notice: Under 35 U.S.C. 154(b), the term of this patent shall be extended for 0 days.

(21) Appl. No.: 08/701,708

(22) Filed: Aug. 22, 1996

(51) Int. Cl.[7] .............................. A61F 2/06; A61L 27/00; A61B 19/00
(52) U.S. Cl. ...................... 623/1.34; 623/1.44; 623/1.46; 606/194; 606/195; 606/198
(58) Field of Search .................................. 623/1, 12, 1.34, 623/1.44, 1.46; 606/194, 195, 198

(56) References Cited

U.S. PATENT DOCUMENTS

| | | |
|---|---|---|
| 4,086,916 * | 5/1978 | Freeman et al. ...................... 600/453 |
| 4,699,611 | 10/1987 | Bowden . |
| 4,943,346 | 7/1990 | Mattelin . |
| 5,047,050 | 9/1991 | Arpesani . |
| 5,067,491 * | 11/1991 | Taylor, II et al. ................... 600/561 |
| 5,104,404 | 4/1992 | Wolff . |
| 5,222,971 | 6/1993 | Willard et al. . |
| 5,269,802 | 12/1993 | Garber . |
| 5,314,444 * | 5/1994 | Gianturco ............................ 606/195 |
| 5,364,354 | 11/1994 | Walker et al. . |
| 5,423,849 | 6/1995 | Engelson et al. . |
| 5,562,728 | 10/1996 | Lazarus et al. . |
| 5,609,629 * | 3/1997 | Fearnot et al. ............................ 623/1 |
| 5,628,787 * | 5/1997 | Mayer ........................................ 623/1 |
| 5,649,951 * | 7/1997 | Davidson ............................. 606/198 |
| 5,674,242 * | 10/1997 | Phan et al. ........................... 606/198 |

FOREIGN PATENT DOCUMENTS

| | | |
|---|---|---|
| 0 380 668 A1 | 4/1989 | (EP) . |
| 0 448 016 * | 9/1991 | (EP) . |
| 448 016 | 9/1991 | (EP) . |
| 0 517 075 A1 | 12/1992 | (EP) . |
| 0 679 372 * | 11/1995 | (EP) . |
| 0 679 373 * | 11/1995 | (EP) . |
| 679 372 | 11/1995 | (EP) . |
| 679 373 | 11/1995 | (EP) . |
| 2677872 A1 | 12/1992 | (FR) . |
| WO 95/03010 | 2/1995 | (WO) . |
| WO/95/03010 | 2/1995 | (WO) . |
| WO 96 24393 | 8/1996 | (WO) . |
| 96 24393 * | 8/1996 | (WO) . |

* cited by examiner

*Primary Examiner*—V Millin
*Assistant Examiner*—Choon P. Koh
(74) *Attorney, Agent, or Firm*—Fulwider Patton Lee & Utecht, LLP

(57) ABSTRACT

The invention relates to coated stents and the method of making them. A stent that is substantially radiolucent is at least partially coated with a radiopaque layer that makes the stent visible under X-ray or fluoroscopy. A protective layer is coated on the stent and the radiopaque layer to protect both from scratches, flaking, and galvanic corrosion, and to improve both blood and bio-compatability.

17 Claims, 2 Drawing Sheets

PROTECTIVE COATING FOR A STENT WITH INTERMEDIATE RADIOPAQUE COATING

BACKGROUND OF THE INVENTION

The invention relates generally to stents, and more particularly to coatings applied to stents to make them radiopaque and coatings to protect the stent and the radiopaque layer.

Stents are useful in the treatment of atherosclerotic stenoses in blood vessels and are generally tubular shaped devices which function to hold open a segment of a blood vessel, artery, heart valve or other body lumen. Stents are particularly suitable for use in supporting and holding open a coronary artery after an atherectomy or angioplasty procedure.

Generally, stents are made from a metal alloy, such as stainless steel, and have a hollow tubular shape with an outer wall surface resembling an open lattice configuration. In some prior art stents, the outer wall surface comprises intersecting wires or struts that are expanded beyond their elastic limit to plastically deform and hold open the body lumen in which they are implanted. Other stents are self-expanding and can be in the form of a coil wire that is biased open.

Stents made from stainless steel, for example, are radiolucent, due in part to the intersecting wires having a diameter of about 0.003 inch or less. Unless the metal or metal alloy used for making the stent has a high atomic weight and density, it is difficult to visualize in vivo during catheter introduction into the vessel, stent deployment, and post-operative diagnosis.

At least one prior art stent has an increased wire diameter, to approximately 0.004 inch, in order to make the stent more radiopaque. The disadvantages of a stent having thicker intersecting wires is a more rigid stent that tracks poorly through a tortuous vessel, is virtually inflexible when tracking on a curved section of vessel, it cannot be implanted easily in a curved section of a vessel, it may not deploy in a uniform cylindrical shape, and it has poor hemodynamics. The latter disadvantage, poor hemodyramics, can result in serious medical complications such as thrombosis.

SUMMARY OF THE INVENTION

The disadvantages of the prior art stents are overcome by the present invention in which a stent is provided that is sufficiently radiopaque, flexible, has a low profile, is substantially non-thrombogenic, and has a protective layer that will eliminate corrosion while still protecting the stent and other layers from mishandling.

The stent of the present invention includes an elongated tubular body that is substantially radiolucent and is formed from, for example, a stainless steel alloy. In order to increase the radiopacity of the stent, without the disadvantages of thicker wires, the stent, or a portion thereof, is coated with a thin radiopaque layer of material having high atomic weight, high density, sufficient surface area and sufficient thickness. With such a coating, the stent is sufficiently radiopaque to be seen with fluoroscopy, yet not so bright as to obstruct the radiopaque dye. This radiopaque layer covers at least a portion of the stent and can be formed from gold, tantalum, platinum, bismuth, iridium, zirconium, iodine, titanium, barium, silver, tin, alloys of these metals, or similar materials.

The radiopaque layer is thin, in one preferred embodiment it is about 1.0 to 50 microns thick. Since the layer is so thin, it is subject to scratching or flaking when the stent is being delivered intraluminally. Accordingly, it is an object of the invention to protect the stent and particularly the radiopaque layer with a more durable protective layer that is resistant to scratching and general mishandling.

Whenever two dissimilar metals are in direct contact, such as a stainless steel stent at least partly covered with a gold radiopaque layer, there is the potential to create the electrochemical reaction that causes galvanic corrosion. The by-product of corrosion (i.e., rust) will not be biocompatible or blood compatible, may cause a toxic response, and may adversely affect adhesion of the radiopaque material. Corrosion will occur if gold and another metal, like stainless steel, are in contact with the same bodily fluid (electrolyte). If the gold coating has any pinhole or has flaked or scratched off the surface, the underlying stainless steel will be exposed to the same fluid. Therefore, a galvanic reaction (battery effect) will occur. The use of a single protective coating covering the entire surface prevents this reaction. This is especially pertinent when the radiopaque layer partially covers the stainless steel stent. The protective layer of the present invention also prevents galvanic corrosion so that the stent is biocompatible.

In one embodiment of the invention, the radiopaque layer can be eliminated by incorporating a radiopaque material, such as barium or titanium oxide in the protective layer. In this embodiment, the stent is visible under fluoroscopy and it is protected by the protective layer, yet it will have a lower profile since it lacks a separate radiopaque layer.

The invention also includes the method of making the stent and applying the radiopaque layer and the protective layer. The radiopaque coating can be applied by dipping, spraying, painting, electroplating, evaporation, plasma vapor deposition, cathodic arc deposition, sputtering, laser welding or fusing, resistance welding, and ion implantation. The protective layer can be applied by dip coating, spray coating, spin coating, plasma deposition, condensation, electrochemically, electrostatically, electroplating, evaporation, plasma vapor deposition, cathodic arc deposition, sputtering, ion implantation, or use of a fluidized bed. The process for applying the radiopaque layer and the protective layer depends upon numerous factors which can include the type of material comprising the layer. These and other advantages of the invention will become more apparent from the following detailed description thereof and the accompanying exemplary drawings.

DETAILED DESCRIPTION OF THE PREFERRED EMBODIMENTS

Figure 1:
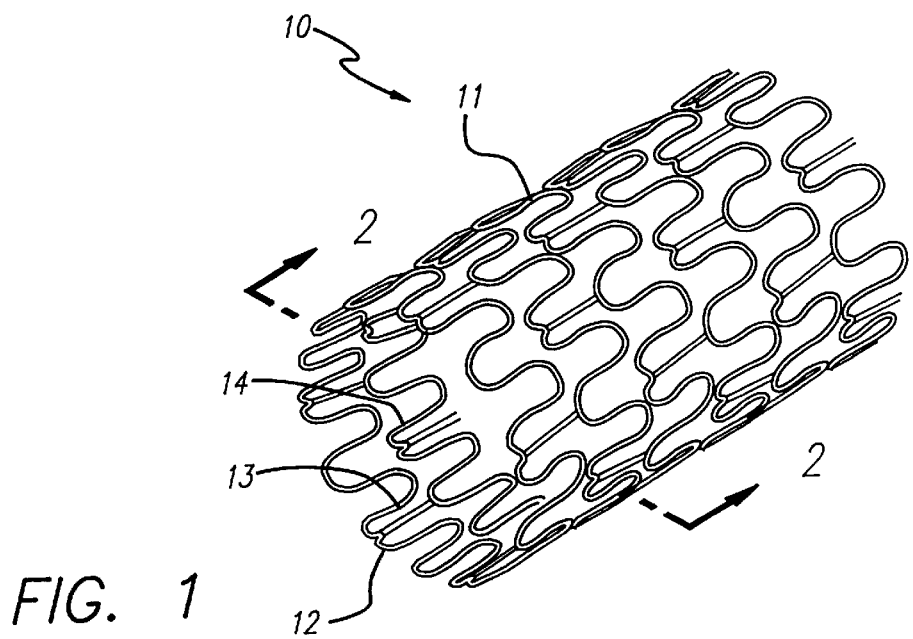
FIG. 1 is a perspective view depicting a stent having an open lattice structure and covered with both a radiopaque layer and a protective layer.

The stent of the present invention is intended for either temporary or permanent deployment in a body lumen such as a coronary artery, carotid artery, vessels in the brain, aorta, peripheral arteries and veins, and the like. The stent also can be deployed in the urethra and other body lumens. The stent is used primarily to support the body lumen so that it remains patent and permits the uninterrupted flow of blood or other body fluids. It is important in the delivery, deployment and post-operative diagnosis that the stent be both visible and remain biocompatible. The stent of the present invention is visible due to a radiopaque layer and it remains biocompatible due its protective layer.

A stent that is made by known etching processes or laser cutting a metal tube, or by winding a metal wire(s), must be sufficiently thick to be radiopaque under X-ray or fluoroscopy in vivo. Generally, current stent designs include an open lattice structure of interwoven wires or struts or coils that are made from stainless steel or other metals or metal alloys that are radiolucent due to a wire thickness or cross-section of about 0.003 inch or less. Unless the metal or alloy used for making the stent has high atomic weight and density, it is difficult to visualize in vivo during catheter introduction into the vessel (artery, vein, urethra, etc.), stent deployment, and post-operative diagnosis. Another solution to increase radiopacity of the stent is to increase the strut or wire cross-section to approximately 0.004 inches, however, this will result in a substantially more rigid stent having poor hemodynamics.

Therefore, coating the stent with a thin layer of material having high atomic weight, high density, sufficient thickness (15 microns or less), and large surface area will have similar effect as thickening the stent. It will make the stent radiopaque sufficiently enough to be seen, but not obstruct the view of radiopaque dye. The coating can be high atomic weight material such as gold, tantalum, platinum, bismuth, iridium or the like. It also can be lower atomic weight material like zirconium iodine, titanium, barium, silver, tin or the like. For the latter-type coatings, a thicker coating may be needed to make the stent sufficiently radiopaque. In either case, a thin coating will allow the stent to remain thin and flexible while maintaining a low stent profile to minimize disruption of blood flow.

On the other hand, thickening the stent or changing the material used for making the stent to a more radiopaque material (i.e., tantalum, gold, etc.) may lead to poor stent performance. A thicker, high profile stent may result in areas of stagnation, turbulence, separation of flow, or other unacceptable fluid dynamics that can promote thrombogenesis. A thicker stent has lower fatigue resistance due to its brittleness. A tantalum stent is brittle and cracks easily. A gold stent will be too expensive and ductile. In the thickness range of less than 0.003 inch, a gold stent will not have sufficient strength to support the artery or body lumen. Both will be too radiopaque (stent made from all tantalum or gold) and obstruct the view of radiopaque dye when it flows through the lumen of the stent. Allowing visualization of the dye flowing through the stent lumen is important for diagnostics. Dye flowing through the stent lumen provides information to the clinician about restenosis, size of artery, size of the stent lumen during and after deployment, presence of dilation or other important parameters necessary for the care of the patient. This avoids the need for post-insertion and post-operative ultrasound detection procedures necessary to determine the diameters of the stent and vessel lumen. Therefore, a thin radiopaque coating is preferred over a stent made entirely from a highly radiopaque material.

Gold is the preferred radiopaque coating because of its high atomic weight and density, both of which contribute to its radiopacity. In addition, gold is a highly ductile metal and therefore, resists cracking when the stent is stressed during deployment or fatigue after deployment. A thin gold coating (less than 15 microns) is sufficient to absorb enough energy to be opaque when exposed to X-rays. Equivalent radiopacity cannot be achieved with a stent made from stainless steel or the like unless the stent is at least twice the thickness. Studies have shown that a 2.0 to 3.0 micron gold coating (or other metal) on a 0.0023 inch-thick 316L stainless steel stent 0.0023 inch diameter of the wires or struts) is sufficient to elevate the radiopacity to make it equivalent in radiopacity to a 0.004 inch-thick 316L stent.

When dissimilar metals come in contact, such as the gold radiopaque coating on a stainless steel stent, the potential to initiate galvanic corrosion exists. This phenomenon occurs when two electrochemically dissimilar metals come in contact with each other. In addition, the radiopaque coating may be less biocompatible than the stent material and may induce thrombosis and sterosis after its deployment. Furthermore, the radiopaque coating is prone to scratching and handling mishaps resulting in scratches, a chipped coating, flaking, or other defects. Surface irregularities on these coatings may act as a loci for unwanted platelet adhesion or cell lysis.

In order to reduce galvanic corrosion and protect the coating, it is essential to coat the outermost surface of the stent (already coated with a radiopaque coating) with a protective coating. The protective coating provides a protective barrier against mishandling, prevents the electrochemical reaction that causes galvanic corrosion, and is blood and tissue compatible. It is thin and flexible such that it will not crack during stent deployment. It will hide any flaws that are on the surface of the stent and prevent any extraordinary events from occurring. In addition, it has lower coefficient of friction than most stent material. A hydrogel layer can also be applied on the inside and/or outside surface of the stent by chemically bonding it to this protective coating. The hydrogel coating can then act as a buffer between the stent and vessel, minimizing vascular injury.

Figure 3:
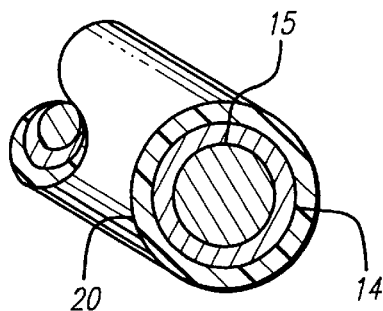
FIG. 3 is a cross-sectional view of one of the wires of the stent of FIG. 2 taken along lines 3—3, depicting the stent wire being coated with a radiopaque layer and a protective layer.
Figure 2:
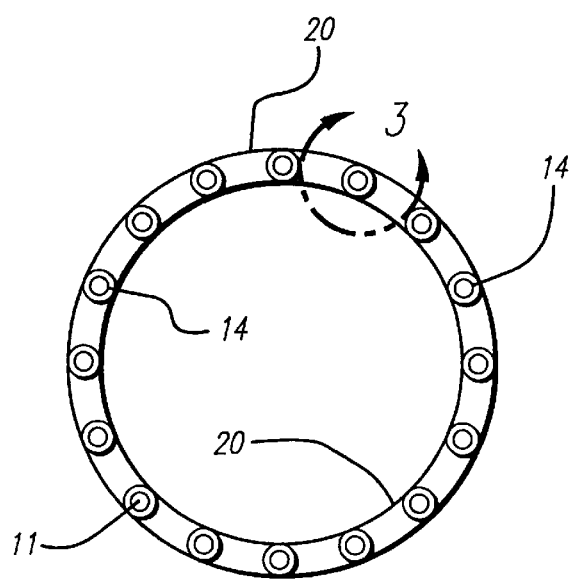
FIG. 2 is a cross-sectional view of the stent of FIG. 1 taken along lines 2—2, depicting the stent covered by a radiopaque layer and a protective layer over the radiopaque layer.

In the preferred embodiment of the invention, as depicted in FIGS. 1–2, stent 10 is generally a cylindrical member having an elongated tubular body 11 with an outer surface 12 and an inner surface 13. When stent 10 is made from a material that is substantially radiolucent, it is important to increase its radiopacity. In order to increase the visibility of stent 10, radiopaque layer 14 is applied to coat all of stent 10, including outer surface 12 and inner surface 13. Typically, stent 10 will he made from a plurality of intersecting struts or wires 15 that can be formed by known methods as described herein. In this embodiment, radiopaque layer 14 is applied so that it covers all portions of struts or wires 15. As is shown in FIG. 3, radiopaque layer 14 surrounds strut 15 so that its radiopacity is ensured. It is preferred that radiopaque layer 14 have a uniform thickness in the range of 1.0 to 50 microns, and more preferably in the range of from 1.5 to 10 microns. If radiopaque layer 14 is too thick, it also may result in stent 10 being too bright under fluoroscopy and it may interfere with the expansion of the stent. Thus, the thickness of radiopaque layer should be uniform and in the preferred thickness ranges, depending upon such factors as the type of metal in the stent, where it will be implanted, the diameter of struts 15, and the like.

In keeping with the preferred embodiment, as shown in FIGS. 1–3, protective layer 20 covers and surrounds radiopaque layer 14 and protects it against scratches, flaking, and other mishandling. Generally, radiopalue layer 14 will be formed from a relatively soft and malleable metal such as gold, and it is subject to scratching and flaking both before it delivered in the patient and after it is mounted on a catheter and delivered intraluminally. Thus, protective layer 20 will provide a durable coating to protect the radiopaque layer.

As will almost always be the case, stent 10 and radiopaque layer 14 will be formed from dissimilar metals which may initiate the chemical reaction leading to galvanic corrosion. Protective layer 20 completely coats radiopaque layer 14 thereby eliminating any likelihood of galvanic corrosion.

Figure 4:
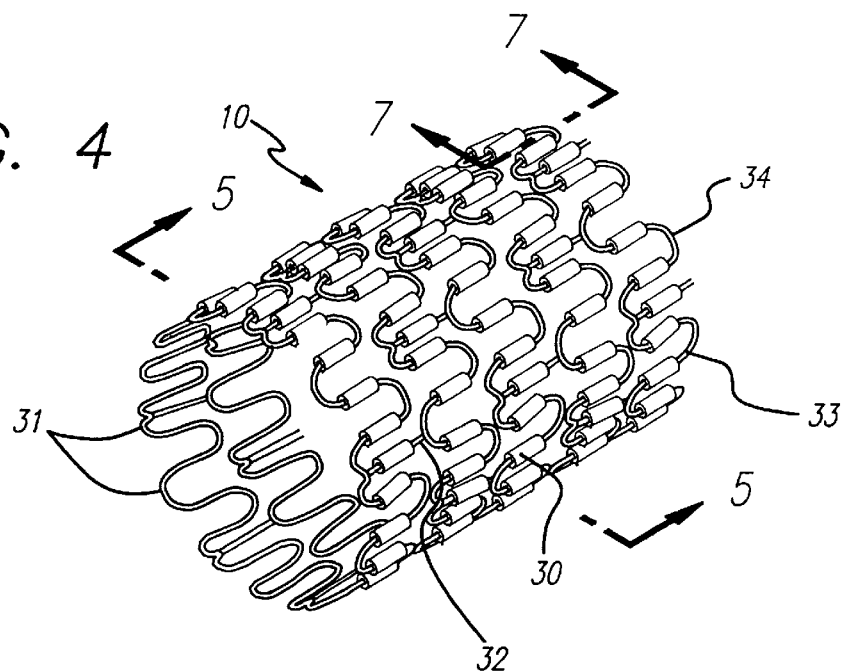
FIG. 4 is a perspective view of a stent having an open lattice structure and being partially covered by a radiopaque layer and completely covered by a protective layer.
Figure 6:
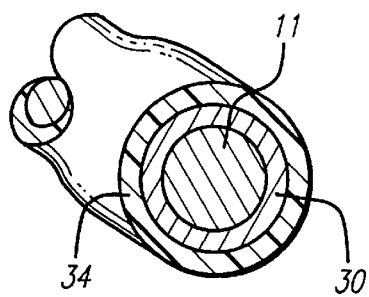
FIG. 6 is a cross-sectional view taken along lines 6—6 of the stent of FIG. 5, depicting a straight portion of a stent wire having a radiopaque layer covered by a protective layer.
Figure 5:
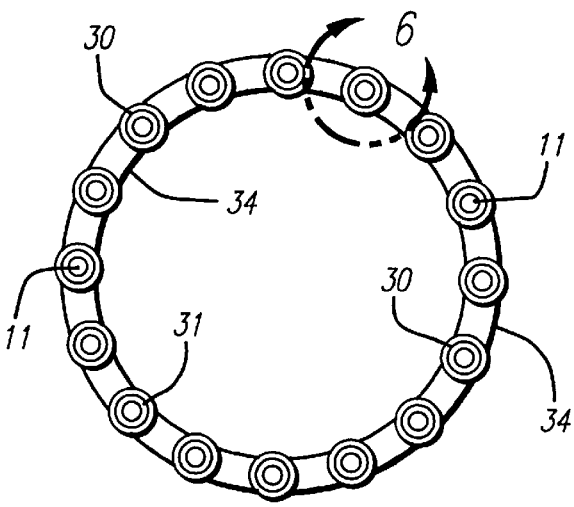
FIG. 5 is a cross-sectional view taken along lines 5—5 of the stent of FIG. 4, depicting a partial radiopaque layer on the stent, covered by a protective layer.

In another preferred embodiment, as seen in FIGS. 4–6, stent 10 is only partially coated by partial radiopaque layer 30. Portions of stent 10 are coated with partial radiopaque layer 30, while stent portion 31, which is curved, is not covered by a radiopaque layer. It is noted that the scale of partial radiopaque layer 30 to the stent struts 33 and protective layer 34 is somewhat cut of proportion for ease of illustration. Typically, as has been demonstrated in experiments, partial radiopaque layer 30 is applied to straight sections 32 of struts 33 so that the stent can be expanded without distortion. Many commercial stents have curved sections and curved struts that will twist and deform if the radiopaque layer is applied to tie curved section, since the radiopaque layer actually adds some rigidity to the stent. Thus, it is preferred that partial radiopaque layer 30 be applied to the non-curved struts of the stent. In other stent configurations, it may not matter where partial radiopaque layer 30 is applied on stent 10. The primary reason for the radiopaque layer is to enhance the visibility of the stent, but it should not interfere with stent expansion.

In the preferred embodiment shown in FIGS. 4–6, stent 10 is coated by protective layer 34 which actually covers stent portion 31 and partial radiopaque layer 30. Protective layer 34 protects partial radiopaque layer 30 as described above, and it eliminates the possibility of galvanic corrosion when stent 10 and partial radiopaque layer 30 are dissimilar metals.

In an alternative embodiment, protective layer 34 covers only partial radiopaque Layer 30 and does not cover those portions of stent 10 where there is no radiopaque coating. Thus, using FIG. 4 as an example, partial radiopaque layer 30 is applied to straight sections 32 and protective coating 34 is selectively applied to cover partial radiopaque layer 30 only.

The radiopaque coating can be made from solid metal (i.e., gold, silver, tin, tantalum, zirconium, platinum, or other metals), ceramic (Zirconia, alumina, zirconium nitrate, titanium nitrite, graphite, pyrolytic carbon, Nedox, or other ceramics), metal/ceramic-filled particles dispersed in a polymer matrix, or other radiopaque material. The radiopaque coating can be coated anywhere or the stent. It can partially cover the stent (one or more bands, longitudinal continuous or discontinuous band, dots, outside surface only, inside surface only, etc.) or fully cover the stent.

In the preferred method of applying radiopaque layer 14 or partial radiopaque layer 30 a radiopaque coating can be applied by dipping, spraying, painting, electroplating, evaporation, plasma vapor deposition, cathodic arc deposition, sputtering, ion implantation, laser welding or fusion, resistance welding, or other methods. The thickness of the radiopaque coating generally is 50 microns or less. The coating can be applied on the inside and/or outside surface of the stent or it can fully encapsulate the stent strut(s).

For instance, a band of gold coating can be placed around the stent at the ends by first completely masking the stent with alkaline or acid resistant mask material (i.e., Microstop, polyesters, acrylic, wax, etc.). The type of mask material depends on the coating process to follow. This is followed by removing the mask preferentially from the stent surface using a laser, sandblaster, or other appropriate methods. Any pattern can be made by selectively removing mask material. The exposed surface (non-masked areas) can then be coated with radiopaque material by, the above-described methods (i.e., electroplating). Other masking techniques are also possible (i.e., physical, chemical, or mechanical). In addition, prefabricated gold markers can also be laser-fused or resistance-welded to the stent at any specific locations. Further details of applying a radiopaque layer to a stent is found in co-pending U.S. Ser. No. 08/564,936.

In the preferred method of applying protective layer 30,34, the biocompatible and blood-compatible protective layer can be polymeric, Parylast®, polymethylene, metallic, or ceramic. A polymeric layer (i.e., Parylene, polycarbonateurethane copolymer, silicone rubber, hydrogels, polyvinyl alcohol, polyvinyl acetate, polycapralactone, urethanes, PHEMA-Acrylic, etc.) can be applied onto the radiopaque-coated stent by dip-coating, spray-coating, spin-coating, plasma deposition, condensation, electrochemically, electrostatically, or other suitable methods. Parylast® is a preferred protective coating and is distributed by Advanced Surface Technology Corp. A metallic coating (i.e., titanium and tantalum) can be applied by electroplating, evaporation, plasma-vapor deposition, cathodic-arc deposition, sputtering, ion implantation, electrostatically, electrochemically, a combination of the above, or the like. A ceramic coating (i.e., zirconium nitrite, pyrolytic carbon, graphite, Nedox, and titanium nitrite) can be applied by the use of a fluidize bed, spraying, plasma-vapor deposition, evaporation, sputtering, electrochemically, electrostatically, a combination of the above, or the like. The thickness of the protective layer preferably is from 0.01 to 25 microns.

Figure 7:
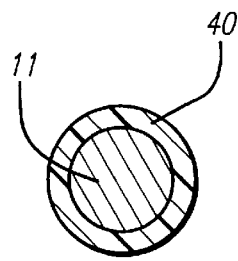
FIG. 7 is a cross-sectional view of the stent of FIG. 5 depicting a stent having a protective layer with a radiopaque agent incorporated in the protective layer.

In an alternative preferred embodiment, as shown in FIG. 7, stent 10 is at least partially covered by protective coating 40 which is itself radiopaque. Protective coating 40 is loaded with radiopaque agents such as barium, titanium oxide, and the like. Further, multiple layers of the protective layer can be applied to the stert where the first layers are loaded with radiopaque agents while the outermost protective layer is not loaded with a radiopaque agent.

In another embodiment, not shown in the drawings, the protective layer is first applied to cover the stent and the radiopaque layer is applied to partially or completely cover the protective layer. In this embodiment, the radiopaque layer is scratch resistant and biocompatible.

A protective layer has been described herein as a mechanical barrier which protects against mishandling, electrochemical reaction that causes galvanic corrosion, and adverse blood and tissue response. It also is important that the protective layer form a conformal coating that will adhere to the stent surface. When there is no adhesion, any stretching and straining of the stent may lead to a rupture of the protective layer, resulting in folds at the strained areas (like elephant skin folds) which may lead to a penetration of blood and tissue causing an adverse response, or causing galvanic corrosion.

Thus, with respect to all of the protective layers disclosed herein, the process to improve adhesion between the protective coating and the substrate (the radiopaque layer) is desired. One such process is to deposit a thin intermediate layer or layers from the silane croup or to plasma deposit a polymer from a gaseous organic such a methane, xylene or gases from the silane or titanate group. A preferred method is to deposit Parylast®, a proprietary coating which incorporates the deposition of an intermediary followed by Parylene C in the same processing chamber. In addition to an intermediary layer, improved adhesion can be attained by reducing the thickness of the protective coating. Thinned coatings tend to be more flexible, especially when the material has a glass transition temperature above room temperature. Thus, thinner coatings adhere better.

Thus, a preferred method is to deposit Parylast®, a proprietary Parylene C coating, which incorporates the addition of an intermediary in the same process chamber.

Another method for improving the adhesion between the protective layer and the radiopaque layer is by acid treatment, sandblasting, or similar methods. These methods allow a mechanical interlocking between the substrate and the protective layer.

Parylast® can be coated at different thicknesses that can vary from 0.00005 inch to 0.0001 inch. It is preferred that the thickness of the Parylast® be at least 0.001 inch in order to minimize the potential for pinhole formation, while maintaining the optimum flexibility (thicker coatings may be too rigid and affect stent expansion). The degree of texture on the substrate may vary from 1 to 250 micrometer average pore sizes. It is preferred that the substrate have a 1–6 micron average pore size. At larger pore sizes, the textured surface is retained on the coated surface after Parylene C or a Parylast® treatment.

After the protective later is applied on the surface, other coatings that may be more blood compatible can also be applied. For example, coatings such as Duroflo, manufactured by Bentley, Photolink Hydrogel, manufactured by BSI, and Photolink Heparin, manufactured by BSI, or similar coatings can enhance the blood compatibility of the stent.

While several particular forms of the invention have been illustrated and described, it will also be apparent that various modifications can be made without departing from the spirit and scope of the invention. Thus, it should be understood that various changes in form, and detail, and application of the present invention may be made without departing from the spirit and scope of this invention.

What is claimed is:

1. A stent for implanting in a body lumen, comprising:
   an elongated tubular body being a substantially radiolucent first metal;
   a radiopaque layer of a second metal different from the first metal covering at least a portion of the elongated tubular body; and
   a protective layer covering the elongated tubular body and radiopaque layer, the protective layer having a thickness effective to reduce the likelihood of galvanic corrosion between the elongated tubular body and the radiopaque layer and to protect the layers from mishandling;
   wherein the protective layer includes a polymeric or a ceramic material.

2. The stent of claim 1, wherein the elongated tubular body is formed from a metallic material selected from the group consisting of stainless steel, nickel-titanium, tantalum, and titanium.

3. The stent of claim 1, wherein the elongated tubular body has a wall surface, made up of a plurality of struts each having a diameter of less than about 0.004 inch.

4. The stent of claim 1, wherein the thickness of the protective layer can vary in thickness on the elongated tubular body from about 0.01 to 25 microns and on the radiopaque layer from about 1.0 to 50 microns.

5. The stent of claim 1, wherein the protective layer is biocompatible and blood compatible.

6. The stent of claim 1, wherein the protective layer is formed from a polymeric material selected from the group consisting of Parylast®, Parylene, polymethylene, polycarbonate-urethane copolymer, silicone rubber, hydrogels, polyvinyl alcohol, polyvinyl acetate, polycapralactone, urethanes, and PHEMA-Acrylic.

7. The stent of claim 1, wherein the protective layer is formed from a metallic material selected from the group consisting of titanium, tantalum, and titanium-alloy.

8. The stent of claim 1, wherein the protective layer is formed from a ceramic material selected from the group consisting of zirconium nitrite, graphite, pyrolytic carbon, Nedox, and titanium nitrite.

9. The stent of claim 1, wherein a second protective coating covers the protective coating to provide further protection against the electrochemical reaction that causes galvanic corrosion.

10. A method for protecting a stent from the electrochemical reaction that causes galvanic corrosion, the method comprising:
    providing an elongated tubular body being substantially radiolucent first metal;
    applying a radiopaque layer of a second metal different from the first metal on at least a portion of the elongated tubular body; and
    applying a protective layer on the elongated tubular body and the radiopaque layer in a thickness effective to reduce the likelihood of galvanic corrosion between the elongated tubular body and the radiopaque layer and to protect the layers from mishandling;
    the protective layer covering all of the radiopaque layer and that portion of the elongated tubular body not covered by the radiopaque layer;
    wherein the protective layer includes a polymeric or a ceramic material.

11. The method of claim 10, wherein the method for applying the radiopaque layer includes dipping, painting, electroplating, evaporation, plasma vapor deposition, cathodic arc deposition, sputtering, laser welding or fusion, resistance welding and ion implantation.

12. The method of claim 10, wherein the method for applying the protective layer includes dipping, spraying, spin coating, plasma deposition, condensation, electrostatically, electrochemically, electroplating, evaporation, plasma vapor deposition, cathodic arc deposition, sputtering, ion implantation, and use of a fluidized bed.

13. A stent for implanting in a body lumen, comprising:
    an elongated tubular body being a substantially radiolucent first metal; and
    a protective layer covering the elongated tubular body, the protective layer having radiopaque means of a second metal different from the first metal for increasing visibility under fluoroscopy, the protective layer having a thickness effective to protect against the electrochemical reaction leading to galvanic corrosion;

wherein the protective layer includes a polymeric or a ceramic material.

14. The stent of claim 13, wherein the radiopaque means includes loading the protective layer material with a radiopaque agent selected from the group consisting of barium, titanium oxide, gold, or other metallic powders or particles.

15. The stent of claim 13, wherein the protective layer is covered by a second protective layer.

16. A stent for implanting in a body lumen, comprising:

an elongated tubular body being a substantially radiolucent first metal;

a protective layer covering the elongated tubular body; and a radiopaque layer of a second metal different from the first metal covering at least a portion of the protective layer so that the stent is visible under fluoroscopic x-ray, the protective layer having a thickness effective to reduce the likelihood of galvanic corrosion between the radiopaque layer and the elongated tubular body;

wherein the protective layer includes a polymeric or a ceramic material.

17. A stent for implanting in a body lumen, comprising:

an elongated tubular body being a substantially radiolucent first metal;

a radiopaque layer of a second metal different from the first metal covering at least a portion of the elongated tubular body; and a protective layer covering at least a portion of the elongated tubular body and having a thickness effective to reduce the likelihood of galvanic corrosion between the elongated tubular body and the radiopaque layer and wherein the protest the layer is biocompatible and blood compatible;

wherein the protective layer includes a polymeric or a ceramic material.

* * * * *

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

Title page,
Under U.S. PATENT DOCUMENTS, add attached 8 page IDC listing U.S. PATENT DOCUMENTS, FOREIGN PATENT DOCUMENTS and OTHER DOCUMENTS.

Column 7, claim 1,
Line 66, after "polymeric", add --, a metallic, --.

Column 8, claim 10,
Line 34, after "being", add -- a --.
Line 47, after "polymeric", add --, a metallic --.

U.S. PATENT DOCUMENTS

| | | |
|---|---|---|
| 3,288,728 | 11/66 | Gorham |
| 3,839,743 | 10/74 | Schwarcz |
| 4,346,028 | 08/82 | Griffith |
| 4,377,030 | 10/89 | Beck et al. |
| 4,633,873 | 01/87 | Dumican et al. |
| 4,656,083 | 04/87 | Hoffman et al. |
| 4,681,110 | 07/87 | Wiktor |
| 4,718,907 | 01/88 | Karwoski et al. |
| 4,722,335 | 02/88 | Vilasli |
| 4,723,549 | 02/98 | Wholey et al. |
| 4,732,152 | 03/88 | Wallsten et al. -- |

FOREIGN PATENT DOCUMENTS

| | | |
|---|---|---|
| WO 91/17789 | 11/91 | PCT |
| WO 93/06792 | 04/93 | PCT |
| 0 540 290 A2 | 05/93 | EPO |
| 0 565 251 A1 | 10/93 | EPO |
| EP-A-0 578 998 | 09/94 | European Patent Office -- |

UNITED STATES PATENT AND TRADEMARK OFFICE
CERTIFICATE OF CORRECTION

PATENT NO.    : 6,174,329 B1
DATED         : January 16, 2001
INVENTOR(S)   : Joseph R. Callol, John Y. Yan It is certified that error appears in the above-identified patent and that said Letters Patent is hereby corrected as shown below:

OTHER DOCUMENTS

Application for U.S. Letters Patent Serial No. 08/355,402 filed December 13, 1994
Application for U.S. Letters Patnet Serial No. 08/233,046 file April 25, 1994
Application for U.S. Letters Patnet Serial No. 08/564,936 (FWC of 08/233,046) filed November 29, 199------------
Application for U.S. Letters Patnet Serial No. 08/234,547 filed April 28, 1994
Application for U.S. Letters Patnet Serial No. 08/559,931 (FWC of 08/234,547) filed November 17, 199------------
Application for U.S. Letters Patnet Serial No. 08/156,268 filed November 22, 1993

U.S. PATENT DOCUMENTS

| | | |
|---|---|---|
| 4,733,665 | 03/88 | Palmaz |
| 4,739,762 | 04/88 | Palmaz |
| 4,768,507 | 09/88 | Fischell et al. |
| 4,776,337 | 10/88 | Palmaz |
| 4,816,339 | 03/89 | Tu et al. |
| 4,830,003 | 05/89 | Wolff et al. |
| 4,856,516 | 08/89 | Hillstead |
| 4,877,030 | 10/89 | Beck et al. |
| 4,878,906 | 11/89 | Lindemann et al. |
| 4,879,135 | 11/89 | Greco et al. |
| 4,886,062 | 12/89 | Wiktor |
| 4,913,141 | 03/90 | Hillstead |
| 4,994,071 | 02/91 | MacGregor |

FOREIGN PATENT DOCUMENTS

| | | |
|---|---|---|
| EP-A-0 604 022 | 01/94 | European Patent Office |
| EP-A-0 621 017 | 10/94 | European Patent Office |
| DE-A-44 07 079 | 09/94 | German Patent Office |
| WO 95/29647 | 11/95 | PCT |

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

OTHER DOCUMENTS

*Union Carbide Technology Letter, New Business Department - Parylene*, Other 1973, No. 7 (8pages)
*Union Carbide, Electronic Materials, Parylene Product*, October 1973, No. 9 (23 pages)
*Union Carbide Technology Letter*, May 1974, No. 11 (12 pages)
*Union Carbide Technology Letter*, October 1975, No. 15 (13 pages)
*Union Carbide, Electronic Materials, Parylene Products*, March 1976, N0. 16 (4 pages)
Eskin, et al., *Growth of Cultured Calf Aortic Smooth Muscle Cells on Cardiovascular Prosthetic Materials*, J. Biomed. Mater . Res., Vol. 10.pp.113-122 (1976)

U.S. PATENT DOCUMENTS

| | | |
|---|---|---|
| 4,994,298 | 01/94 | Yasuda |
| 5,019,090 | 05/91 | Pinchuk |
| 5,053,048 | 10/91 | Pinchuk |
| 5,059,211 | 10/91 | Stack et al. |
| 5,062,829 | 11/91 | Pryor et al. |
| 5,084,065 | 01/92 | Weldon et al. |
| 5,085,629 | 02/94 | Goldberg et al. |
| 5,102,417 | 04/92 | Palmaz |
| 5,104,404 | 04/92 | Wolff |
| 5,108,755 | 04/92 | Daniels et al. |
| 5,116,365 | 04/92 | Hillstead |

OTHER DOCUMENTS

Loeb, et al. *Parylene as a Chronically Stable, Reproducible Microelectrode Innsulator*, IEEE Transactions on Biomedical Engineering, March 1977 (pp.121-128)

*Union Carbide, Electronic Materials, Parylene Products*, August 1977, No. 18 (7 pages)
*Union Carbide, Electronic Materials, Parylene Products*, October 1977, No.1 Revision 2 (7 pages)
*Union Carbide, Electronic Materials, Parylene Products*, October 1977, No.2 Revision 1 (9 pages)
*Union Carbide, Electronic Materials, Parylene Products*, October 1977, No.3 (21 pages)

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

OTHER DOCUMENTS cont'd

*Union Carbide, Electronic Materials, Parylene Products,* October 1977, No.4 (13 pages)
*Union Carbide, Electronic Materials, Parylene Products,* October 1977, No.6 (12 pages)

U.S. PATENT DOCUMENTS

| | | |
|---|---|---|
| 5,123,917 | 06/92 | Lee |
| 5,133,732 | 07/92 | Wiktor |
| 5,135,536 | 08/92 | Hillstead |
| 5,156,623 | 10/92 | Hakamatsuka et al. |
| 5,163,951 | 11/92 | Pinchuk et al. |
| 5,163,952 | 11/92 | Froix |
| 5,163,958 | 11/92 | Pinchuk |
| 5,192,311 | 03/93 | King et al. |
| 5,197,977 | 03/93 | Hoffman, Jr. et al. |
| 5,223,913 | 07/93 | Pinckuk |
| 5,234,456 | 08/93 | Silvestrini |

OTHER DOCUMENTS

*Union Carbide, Electronic Materials, Parylene Products,* October 1977, No. 7 Revision 1 (8 pages)
*Union Carbide, Electronic Materials, Parylene Products,* October 1977, No. 8 Edited (19 pages)
*Union Carbide, Electronic Materials, Parylene Products,* October 1977, No.10 (50 pages)
*Union Carbide, Electronic Materials, Parylene Products,* October 1977, No. 11 (12 pages)
*Union Carbide, Electronic Materials, Parylene Products,* October 1977, No. 12 Revision 1 (6 pages)
*Union Carbide, Electronic Materials, Parylene Products,* October 1977, No. 13 Revision 1 (7 pages)

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

U.S. PATENT DOCUMENTS

| | | |
|---|---|---|
| 5,234,457 | 08/93 | Andersen |
| 5,236,447 | 08/93 | Kubo et al. |
| 5,279,594 | 01/94 | Jackson |
| 5,282,823 | 02/94 | Schwartz et al. |
| 5,282,860 | 02/94 | Matsuno et al. |
| 5,289,831 | 03/94 | Bosley |
| 5,290,271 | 03/94 | Jernberg |
| 5,304200 | 04/94 | Spaulding |
| 5,306,286 | 04/94 | Stack et al. |
| 5,314,472 | 05/94 | Fontaine |
| 5,330,500 | 07/94 | Song |

OTHER DOCUMENTS

*Union Carbide, Electronic Materials, Parylene Products*, October 1977, 14, Revision 1 (11 pages)
*Union Carbide, Electronic Materials, Parylene Products*, October 1977, 15, Revision 1 (8 pages)
*Union Carbide, Electronic Materials, Parylene Products*, October 1977, 17, Revision 1 (11 pages)
*ISEEE Transactions on Biomedical Engineering*, BME-27, No. 11, November 1980 (5 pages)

Sadhir, et al., *The Adhesion of Glow-Discharge Polymers, Silastic and Parylene to Implantable Platinum Electrodes: Results of Tensile Pull Tests After Exposure to Isotonic Sodium Chloride*, October 1981, Vol. 2, Biomaterials (pp. 239-243)

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

U.S. PATENT DOCUMENTS

| | | |
|---|---|---|
| 5,342,348 | 08/94 | Kaplan |
| 5,342,621 | 08/94 | Eury |
| 5,356,433 | 10/94 | Rowland et al. |
| 5,360,443 | 11/94 | Barone et al. |
| 5,383,927 | 01/95 | DeGoicoechea et al. |
| 5,389,106 | 02/95 | Tower |

OTHER PATENT DOCUMENTS

Hahn, et al. *Glow Discharge Polymers as Coatings for Implanted Devices*, John M. Dlaton Research Center, University of Missouri-Columbia and the Graduate Center for Materials Research, 1981 (pp. 109-113)
*Union Carbide, Electrode Material, Parylene Products*, January 18, 1982, No. 5. Revision 4 (17 pages)
Hahn, et al., *Biocompatibility of Glow-Discharge-Polymerized Films and Vacuum-Deposited Parylene*, Journal of Applied Polymer Science: Applied Polymer Symposium 38, 55-64 (1984)
Casper, et al. *Fiber-Reinforced Absorbable Composite for Orthopedic Surgery*, Polymeric Materials Science and Engineering. Proceedings of the ACS Division of Polymeric Materials: Science and Engineering, Volumn 53, Fall Meeting 1985
Kelly, et al. *Totally Resorbable High-Strength Composite Material*. Advances in Biomedical Polymers, Edited by Charles G. Gebelein (1987)
Yuen, et al., *Tissue Response to Potential Neuroprosthetic Materials Implanted Subdurally*, Biomaterials March 1987. Vol. 8 (pp. 57-62)

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

OTHER DOCUMENTS

Nichols, et al. *Elecrical Insulation of Implantable Devices by Composite Polymer Coatings*, Dalton Research Center University of Missouri, 1987
Schmidt, et al., *Long-Term Implants of Parylene-C Coated Microelectrodes*, Medical & Biological Engineering & Computing, January 1988 (pp. 96-101)
Olson, *Parylene, a Biostable Coating for Medical Applications*, for NOVA TRAN Parylene Coating Services (July 25, 1988; November 14, 1988)
Beach, et al. *Xylyene Polymers*, Encyclopedia of Polymer Science and Engineering, Vol. Second Edition, pp. 990-1025, 1989
Muller et al. *Advances in Coronary Angioplasty: Endovascular Stents*, Coronary Artery Disease, Jul/Aug 1990, Vol. 1, No. 4
Loh, et al. *Plasma Enhanced Parylene Deposition*, Antec. Pp 1099-1103, 1991
Gebelein, et al., *Biomedical and Dental Applications of Polymers*, Polymer Science and Technoloy, Vol. 14 (No date) (pp. 143-161
Wong, M.D., et al., *An Update on Coronary Stents*, Cardio, February 1992
*The Parylene Press* (A Publication of Specialty Coating Systems, Inc.), Winter 1992 (7 pages)
Charlson, et al., *Temperature Selective Deposition of Parylene-C*. IEEE Transactions of Biomedical Engineering, Vol. 39, No. 2, February 1992 (pp. 202-206)
Bull: *Parylene Coating for Medical Applications*, Medical Product Manufacturing News, March 1993 (2 pages)
*The Parylene Press* (A Publication of Specialty Coating Systems, Inc.), Spring 1993 (6 pages)
*The Parylene Press* (A Publication of Specialty Coating Systems, Inc.), Summer 1993 (4 pages)
*Information Regarding Parylene-C Coating for ACS Metal Stent*, In-House Memorandum from Ed Newton to Joe Callol, Mike Clayman, Dennis Houlsby and Joe Tartaglia, October 15, 1993 attaching *Parylene, a Biostable Coating for Medical Application by* Roger Olson
Moody: *Vacuum Coating Ultrasonic Transducers, Sensors, December 1993 (1 page)
Union Carbide A-174 Silane*, Sales Brochure, Union Carbide Adhesion Promoters, January 1968 (5pages)
*Parylene Conformal Coatings Specifications and Properties*, Sales Brochure, Union Carbide Speciality Coating Systems (12 pages)

UNITED STATES PATENT AND TRADEMARK OFFICE
CERTIFICATE OF CORRECTION

PATENT NO.    : 6,174,329, B1
DATED         : January 16, 2001
INVENTOR(S)   : Joseph R. Callol, John Y. Yan It is certified that error appears in the above-identified patent and that said Letters Patent is hereby corrected as shown below:

OTHER DOCUMENTS

*Parylene Environmentally Compatible Conformal Coatings for Electronic Components Assemblies and Presision Parts*, Brochure, Union Carbide Electronics Division (14 pages)
*Parylene and Nova Tran™ Parylene Coating Services, for Unmatched Conformal Coating Performace*, Brochure, Union Carbide Specialty Coating Systems (21 pages)
*Repair and Recoating of Parylene Coated Printed Circuit Boards*, Brochure, Union Carbide Specialty Coating Systems (15 pages)
*Nova Tran™ Custom Coating Services, Parylene Conformal Coating*, Brochure, Union Carbide (8 pages)
*Parylene, a Biostable Coating for Medical Applications*, Brochure, Union Carbide Specialty Coating Systems (6 pages)
*Typical Parylene Properties*, Printout, Para Tech Coating Company; *Lab Top® Parylene Deposition System Model 3000*, Sales Brochure, Para Tech Coating Company (7 pages)

Signed and Sealed this

Fifth Day of February, 2002

*Attest:*

JAMES E. ROGAN
*Attesting Officer*       Director of the United States Patent and Trademark Office

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

Title page,
Under U.S. PATENT DOCUMENTS, add attached 8 page IDC listing U.S. PATENT DOCUMENTS, FOREIGN PATENT DOCUMENTS and OTHER DOCUMENTS.

Column 7, claim 1,
Line 66, after "polymeric", add --, a metallic, --.

Column 8, claim 10,
Line 34, after "being", add -- a --.
Line 47, after "polymeric", add --, a metallic --.

U.S. PATENT DOCUMENTS

| | | |
|---|---|---|
| 3,288,728 | 11/66 | Gorham |
| 3,839,743 | 10/74 | Schwarcz |
| 4,346,028 | 08/82 | Griffith |
| 4,377,030 | 10/89 | Beck et al. |
| 4,633,873 | 01/87 | Dumican et al. |
| 4,656,083 | 04/87 | Hoffman et al. |
| 4,681,110 | 07/87 | Wiktor |
| 4,718,907 | 01/88 | Karwoski et al. |
| 4,722,335 | 02/88 | Vilasli |
| 4,723,549 | 02/88 | Wholey et al. |
| 4,732,152 | 03/88 | Wallsten et al. -- |

FOREIGN PATENT DOCUMENTS

| | | |
|---|---|---|
| WO 91/17789 | 11/91 | PCT |
| WO 93/06792 | 04/93 | PCT |
| 0 540 290 A2 | 05/93 | EPO |
| 0 565 251 A1 | 10/93 | EPO |
| EP-A-0 578 998 | 06/94 | European Patent Office -- |

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

OTHER DOCUMENTS

Application for U.S. Letters Patent Serial No. 08/355,402 filed December 13, 1994
Application for U.S. Letters Patent Serial No. 08/233,046 file April 25, 1994
Application for U.S. Letters Patent Serial No. 08/564,936 (FWC of 08/233,046) filed November 29, 1995
Application for U.S. Letters Patent Serial No. 08/234,547 filed April 28, 1994
Application for U.S. Letters Patent Serial No. 08/559,931 (FWC of 08/234,547) filed November 17, 1995
Application for U.S. Letters Patent Serial No. 08/156,268 filed November 22, 1993

U.S. PATENT DOCUMENTS

| | | |
|---|---|---|
| 4,733,665 | 03/88 | Palmaz |
| 4,739,762 | 04/88 | Palmaz |
| 4,768,507 | 09/88 | Fischell et al. |
| 4,776,337 | 10/88 | Palmaz |
| 4,816,339 | 03/89 | Tu et al. |
| 4,830,003 | 05/89 | Wolff et al. |
| 4,856,516 | 08/89 | Hillstead |
| 4,877,030 | 10/89 | Beck et al. |
| 4,878,906 | 11/89 | Lindemann et al. |
| 4,879,135 | 11/89 | Greco et al. |
| 4,886,062 | 12/89 | Wiktor |
| 4,913,141 | 03/90 | Hillstead |
| 4,994,071 | 02/91 | MacGregor |

FOREIGN PATENT DOCUMENTS

| | | |
|---|---|---|
| EP-A-0 604 022 | 01/94 | European Patent Office |
| EP-A-0 621 017 | 10/94 | European Patent Office |
| DE-A-44 07 079 | 09/94 | German Patent Office |
| WO 95/29647 | 11/95 | PCT |

UNITED STATES PATENT AND TRADEMARK OFFICE
CERTIFICATE OF CORRECTION

PATENT NO. : 6,174,329 B1  
DATED : January 16, 2001  
INVENTOR(S) : Joseph R. Callol, John Y. Yan Page 3 of 8

It is certified that error appears in the above-identified patent and that said Letters Patent is hereby corrected as shown below:

OTHER DOCUMENTS

*Union Carbide Technology Letter, New Business Department - Parylene,* October 1973, No. 7 (8pages)
*Union Carbide, Electronic Materials, Parylene Product,* October 1973, No. 9 (23 pages)
*Union Carbide Technology Letter,* May 1974, No. 11 (12 pages)
*Union Carbide Technology Letter,* October 1975, No. 15 (13 pages)
*Union Carbide, Electronic Materials, Parylene Products,* March 1976, N0. 16 (4 pages)
Eskin, et al., *Growth of Cultured Calf Aortic Smooth Muscle Cells on Cardiovascular Prosthetic Materials,* J. Biomed. Mater . Res., Vol. 10, pp.113-122 (1976)

U.S. PATENT DOCUMENTS

| | | |
|---|---|---|
| 4,994,298 | 02/91 | Yasuda |
| 5,019,090 | 05/91 | Pinchuk |
| 5,053,048 | 10/91 | Pinchuk |
| 5,059,211 | 10/91 | Stack et al. |
| 5,062,829 | 11/91 | Pryor et al. |
| 5,084,065 | 01/92 | Weldon et al. |
| 5,085,629 | 02/92 | Goldberg et al. |
| 5,102,417 | 04/92 | Palmaz |
| 5,104,404 | 04/92 | Wolff |
| 5,108,755 | 04/92 | Daniels et al. |
| 5,116,365 | 05/92 | Hillstead |

OTHER DOCUMENTS

Loeb, et al. *Parylene as a Chronically Stable, Reproducible Microelectrode Innsulator,* IEEE Transactions on Biomedical Engineering, March 1977 (pp.121-128)

*Union Carbide, Electronic Materials, Parylene Products,* August 1977, No. 18 (7 pages)
*Union Carbide, Electronic Materials, Parylene Products,* October 1977, No. 1 Revision 2 (7 pages)
*Union Carbide, Electronic Materials, Parylene Products,* October 1977, No. 2 Revision 1 (9 pages)
*Union Carbide, Electronic Materials, Parylene Products,* October 1977, No. 3

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

OTHER DOCUMENTS cont'd

*Union Carbide, Electronic Materials, Parylene Products*, October 1977, No. 4 (13 pages)
*Union Carbide, Electronic Materials, Parylene Products*, October 1977, No. 6 (12 pages)

U.S. PATENT DOCUMENTS

| | | |
|---|---|---|
| 5,123,917 | 06/92 | Lee |
| 5,133,732 | 07/92 | Wiktor |
| 5,135,536 | 08/92 | Hillstead |
| 5,156,623 | 10/92 | Hakamatsuka et al. |
| 5,163,951 | 11/92 | Pinchuk et al. |
| 5,163,952 | 11/92 | Froix |
| 5,163,958 | 11/92 | Pinchuk |
| 5,192,311 | 03/93 | King et al. |
| 5,197,977 | 03/93 | Hoffman, Jr. et al. |
| 5,226,913 | 07/93 | Pinckuk |
| 5,234,456 | 08/93 | Silvestrini |

OTHER DOCUMENTS

*Union Carbide, Electronic Materials, Parylene Products*, October 1977, No. 7 Revision 1 (8 pages)
*Union Carbide, Electronic Materials, Parylene Products*, October 1977, No. 8 Edited (19 pages)
*Union Carbide, Electronic Materials, Parylene Products*, October 1977, No.10 (50 pages)
*Union Carbide, Electronic Materials, Parylene Products*, October 1977, No. 11 (12 pages)
*Union Carbide, Electronic Materials, Parylene Products*, October 1977, No. 12 Revision 1 (6 pages)
*Union Carbide, Electronic Materials, Parylene Products*, October 1977, No. 13 Revision 1 (7 pages)

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

U.S. PATENT DOCUMENTS

| | | |
|---|---|---|
| 5,234,457 | 08/93 | Andersen |
| 5,236,447 | 08/93 | Kubo et al. |
| 5,279,594 | 01/94 | Jackson |
| 5,282,823 | 02/94 | Schwartz et al. |
| 5,282,860 | 02/94 | Matsuno et al. |
| 5,289,831 | 03/94 | Bosley |
| 5,290,271 | 03/94 | Jernberg |
| 5,304,200 | 04/94 | Spaulding |
| 5,306,286 | 04/94 | Stack et al. |
| 5,314,472 | 05/94 | Fontaine |
| 5,330,500 | 07/94 | Song |

OTHER DOCUMENTS

*Union Carbide, Electronic Materials, Parylene Products*, October 1977, No. 14, Revision 1
(11 pages)
*Union Carbide, Electronic Materials, Parylene Products*, October 1977, No. 15, Revision 1
(8 pages)
*Union Carbide, Electronic Materials, Parylene Products*, October 1977, No. 17, Revision 1
(11 pages)
*ISEEE Transactions on Biomedical Engineering*, BME-27, No. 11, November 1980
(5 pages)

Sadhir, et al., *The Adhesion of Glow-Discharge Polymers, Silastic and Parylene to Implantable Platinum Electrodes: Results of Tensile Pull Tests After Exposure to Isotonic Sodium Chloride*, October 1981, Vol. 2, Biomaterials (pp. 239-243)

UNITED STATES PATENT AND TRADEMARK OFFICE
CERTIFICATE OF CORRECTION

PATENT NO.    : 6,174,329 B1
DATED         : January 16, 2001
INVENTOR(S)   : Joseph R. Callol, John Y. Yan It is certified that error appears in the above-identified patent and that said Letters Patent is hereby corrected as shown below:

U.S. PATENT DOCUMENTS

| | | |
|---|---|---|
| 5,342,348 | 08/94 | Kaplan |
| 5,342,621 | 08/94 | Eury |
| 5,356,433 | 10/94 | Rowland et al. |
| 5,360,443 | 11/94 | Barone et al. |
| 5,383,927 | 01/95 | DeGoicoechea et al. |
| 5,389,106 | 02/95 | Tower |

OTHER PATENT DOCUMENTS

Hahn, et al. *Glow Discharge Polymers as Coatings for Implanted Devices*, John M. Dlaton Research Center, University of Missouri-Columbia and the Graduate Center for Materials Research, 1981 (pp. 109-113)

*Union Carbide, Electrode Material, Parylene Products*, January 18, 1982, No. 5. Revision 4 (17 pages)

Hahn, et al., *Biocompatibility of Glow-Discharge-Polymerized Films and Vacuum-Deposited Parylene*, Journal of Applied Polymer Science: Applied Polymer Symposium 38, 55-64 (1984)

Casper, et al. *Fiber-Reinforced Absorbable Composite for Orthopedic Surgery*, Polymeric Materials Science and Engineering. Proceedings of the ACS Division of Polymeric Materials: Science and Engineering, Volumn 53, Fall Meeting 1985

Kelly, et al. *Totally Resorbable High-Strength Composite Material.* Advances in Biomedical Polymers, Edited by Charles G. Gebelein (1987)

Yuen, et al., *Tissue Response to Potential Neuroprosthetic Materials Implanted Subdurally*, Biomaterials March 1987. Vol. 8 (pp. 57-62)

UNITED STATES PATENT AND TRADEMARK OFFICE
CERTIFICATE OF CORRECTION

PATENT NO. : 6,174,329 B1
DATED : January 16, 2001
INVENTOR(S) : Joseph R. Callol, John Y. Yan It is certified that error appears in the above-identified patent and that said Letters Patent is hereby corrected as shown below:

OTHER DOCUMENTS

Nichols, et al. *Elecrical Insulation of Implantable Devices by Composite Polymer Coatings*, Dalton Research Center University of Missouri, 1987
Schmidt, et al., *Long-Term Implants of Parylene-C Coated Microelectrodes*, Medical & Biological Engineering & Computing, January 1988 (pp. 96-101)
Olson, *Parylene, a Biostable Coating for Medical Applications*, for NOVA TRAN Parylene Coating Services (July 25, 1988; November 14, 1988)
Beach, et al. *Xylyene Polymers*, Encyclopedia of Polymer Science and Engineering, Vol. 17 Second Edition, pp. 990-1025, 1989
Muller et al. *Advances in Coronary Angioplasty: Endovascular Stents*, Coronary Artery Disease, Jul/Aug 1990, Vol. 1, No. 4
Loh, et al. *Plasma Enhanced Parylene Deposition*, Antec. Pp 1099-1103, 1991
Gebelein, et al., *Biomedical and Dental Applications of Polymers*, Polymer Science and Technoloy, Vol. 14 (No date) (pp. 143-161
Wong, M.D., et al., *An Update on Coronary Stents*, Cardio, February 1992
*The Parylene Press* (A Publication of Specialty Coating Systems, Inc.), Winter 1992 (7 pages)
Charlson, et al., *Temperature Selective Deposition of Parylene-C*, IEEE Transactions on Biomedical Engineering, Vol. 39, No. 2, February 1992 (pp. 202-206)
Bull: *Parylene Coating for Medical Applications*, Medical Product Manufacturing News, March 1993 (2 pages)
*The Parylene Press* (A Publication of Specialty Coating Systems, Inc.), Spring 1993 (6 pages)
*The Parylene Press* (A Publication of Specialty Coating Systems, Inc.), Summer 1993 (4 pages)
*Information Regarding Parylene-C Coating for ACS Metal Stent*, In-House Memorandum from Ed Newton to Joe Callol, Mike Clayman, Dennis Houlsby and Joe Tartaglia, October 15, 1993 attaching *Parylene, a Biostable Coating for Medical Application* by Roger Olson
Moody: *Vacuum Coating Ultrasonic Transducers, Sensors*, December 1993 (1 page)
*Union Carbide A-174 Silane*, Sales Brochure, Union Carbide Adhesion Promoters, January 1968 (5pages)
*Parylene Conformal Coatings Specifications and Properties*, Sales Brochure, Union Carbide Speciality Coating Systems (12 pages)

UNITED STATES PATENT AND TRADEMARK OFFICE
CERTIFICATE OF CORRECTION

PATENT NO. : 6,174,329, B1
DATED : January 16, 2001
INVENTOR(S) : Joseph R. Callol, John Y. Yan It is certified that error appears in the above-identified patent and that said Letters Patent is hereby corrected as shown below:

OTHER DOCUMENTS

*Parylene Environmentally Compatible Conformal Coatings for Electronic Components Assemblies and Presision Parts*, Brochure, Union Carbide Electronics Division (14 pages)
*Parylene and Nova Tran™ Parylene Coating Services, for Unmatched Conformal Coating Performace*, Brochure, Union Carbide Specialty Coating Systems (21 pages)
*Repair and Recoating of Parylene Coated Printed Circuit Boards*, Brochure, Union Carbide Specialty Coating Systems (15 pages)
*Nova Tran™ Custom Coating Services, Parylene Conformal Coating*, Brochure, Union Carbide (8 pages)
*Parylene, a Biostable Coating for Medical Applications*, Brochure, Union Carbide Specialty Coating Systems (6 pages)
*Typical Parylene Properties*, Printout, Para Tech Coating Company; *Lab Top® Parylene Deposition System Model 3000*, Sales Brochure, Para Tech Coating Company (7 pages)

Signed and Sealed this

Nineteenth Day of February, 2002

JAMES E. ROGAN
*Director of the United States Patent and Trademark Office*

*Attest:*

*Attesting Officer*